(12) United States Patent
Kim et al.

(10) Patent No.: US 11,862,301 B2
(45) Date of Patent: Jan. 2, 2024

(54) TECHNIQUE FOR TRAINING DEMENTIA IDENTIFICATION MODEL BASED ON TEST RESULT DATA

(71) Applicant: HAII CO, LTD., Seoul (KR)

(72) Inventors: Ho Yung Kim, Seoul (KR); Geon Ha Kim, Seoul (KR); Bo Hee Kim, Seoul (KR); Dong Han Kim, Seoul (KR); Hye Bin Hwang, Incheon (KR); Chan Yeong Park, Seoul (KR); Ji An Choi, Seoul (KR); Bo Ri Kim, Seoul (KR)

(*) Notice: Subject to any disclaimer, the term of this patent is extended or adjusted under 35 U.S.C. 154(b) by 66 days.

(21) Appl. No.: 17/897,082

(22) Filed: Aug. 26, 2022

(65) Prior Publication Data
US 2023/0215520 A1    Jul. 6, 2023

(30) Foreign Application Priority Data
Jan. 5, 2022    (KR) .................. 10-2022-0001427

(51) Int. Cl.
*G16H 10/20*    (2018.01)
*G16H 10/60*    (2018.01)

(52) U.S. Cl.
CPC ............. *G16H 10/20* (2018.01); *G16H 10/60* (2018.01)

(58) Field of Classification Search
CPC .............................. G16H 10/20; G16H 10/60
USPC ........................................................ 705/2
See application file for complete search history.

(56) References Cited

U.S. PATENT DOCUMENTS

| | | | | |
|---|---|---|---|---|
| 6,471,521 B1* | 10/2002 | Dornbush | ............ | G09B 5/14 434/353 |
| 2013/0268472 A1* | 10/2013 | Lin | ............ | G06N 3/084 706/15 |
| 2016/0155355 A1* | 6/2016 | Merzenich | ............ | A63F 13/80 434/236 |
| 2021/0235163 A1* | 7/2021 | Hirsch | ............ | H04N 21/812 |
| 2021/0343376 A1* | 11/2021 | Neumann | ............ | G06Q 50/01 |

FOREIGN PATENT DOCUMENTS

| | | |
|---|---|---|
| KR | 1020120110762 A | 10/2012 |
| KR | 1020190021896 A | 3/2019 |
| KR | 1020190135908 A | 12/2019 |
| KR | 1020190136313 A | 12/2019 |
| KR | 102257291 B1 | 5/2021 |
| KR | 102314213 B1 | 10/2021 |

(Continued)

OTHER PUBLICATIONS

Memorize available at https://memorize.link/en/stroop/test captured by the Wayback Machine prior to the effective filing date of the claimed invention, e.g., Oct. 19, 2021 (hereinafter Memorize) (Year: 2021).*

(Continued)

*Primary Examiner* — Jonathon A. Szumny
*Assistant Examiner* — Christopher B Wehrly
(74) *Attorney, Agent, or Firm* — Aird & McBurney LP

(57) ABSTRACT

Disclosed is a method of training the dementia identification model. More particularly, the method may include obtaining test result data through at least one of a first task related to Stroop test, a second task related to a computational power test, and a third task related to a memory test; and labeling the test result data with a score value to train the dementia identification model.

16 Claims, 5 Drawing Sheets

(56) References Cited

FOREIGN PATENT DOCUMENTS

| | | |
|---|---|---|
| KR | 102321197 B1 | 11/2021 |
| KR | 20210155335 A | 12/2021 |

OTHER PUBLICATIONS

"The Counting Stroop And The Interference Effect." ukessays.com. Nov. 2018. UKEssays. Oct. 2022 https://www.ukessays.com/essays/psychology/the-counting-stroop-and-the-interference-effect-psychology-essay.php?vref=1 (hereinafter UKEssays) (Year: 2018).*

"Lumosity Top That." YouTube. Published Sep. 10, 2020. Available at https://www.youtube.com/watch?v=W4_7OUg9W9Y (hereinafter Luminosity) (Year: 2020).*

* cited by examiner (a)

(b)

TECHNIQUE FOR TRAINING DEMENTIA IDENTIFICATION MODEL BASED ON TEST RESULT DATA

TECHNICAL FIELD

The present disclosure relates to a technique for training a dementia identification model, and more particularly to a device for training a dementia identification model using test result data obtained through at least one test and a method thereof.

BACKGROUND ART

Alzheimer's disease (AD), which is a brain disease caused by aging, causes progressive memory impairment, cognitive deficits, changes in individual personality, etc. In addition, dementia refers to a state of persistent and overall cognitive function decline that occurs when a person who has led a normal life suffers from damage to brain function due to various causes. Here, cognitive function refers to various intellectual abilities such as memory, language ability, temporal and spatial understanding ability, judgment ability, and abstract thinking ability. Each cognitive function is closely related to a specific part of the brain. The most common form of dementia is Alzheimer's disease.

Various methods have been proposed for diagnosing Alzheimer's disease, dementia, or mild cognitive impairment. For example, a method of diagnosing Alzheimer's disease or mild cognitive impairment using the expression level of miR-206 in the olfactory tissue, a method for diagnosing dementia using a biomarker that characteristically increases in blood, and the like are known.

However, since special equipment or tests necessary for biopsy are required so as to use miR-206 in the olfactory tissue, and blood from a patient should be collected by an invasive method so as to use biomarkers in blood, there is a disadvantage that the patient's rejection feeling is relatively large.

Therefore, there is an urgent need for development of a dementia diagnosis method where patients hardly feel rejection without a separate special equipment or examination.

SUMMARY OF THE DISCLOSURE

Technical Problem

Therefore, the present disclosure has been made in view of the above problems, and it is one object of the present disclosure to train a dementia identification model with an accurate dementia diagnosis method where patients hardly feel rejection.

It will be understood that technical problems of the present disclosure are not limited to the aforementioned problem and other technical problems not referred to herein will be clearly understood by those skilled in the art from the description below.

Technical Solution

In accordance with an aspect of the present invention, the above and other objects can be accomplished by the provision of a method of training a dementia identification model by at least one processor of a device, the method including: obtaining test result data through at least one of a first task related to Stroop test, a second task related to a computational power test, and a third task related to a memory test; and labeling the test result data with a score value to train the dementia identification model.

In accordance with some embodiments of the present disclosure, the first task may include: a first sub-task that causes a test device of a test user to display a first number of numeric texts in a first region while interworking with displaying a first button for displaying a first numeral indicating the first number on a second region; and at least one second button for displaying a number different from the first number; and a second sub-task that determines whether an answer is correct according to a first selection input of selecting any one of the first button and the at least one second button.

In accordance with some embodiments of the present disclosure, the first task may perform the first sub-task and the second sub-task a preset number of times while changing the first number and the numeric texts.

In accordance with some embodiments of the present disclosure, the second sub-task may include: an operation of determining an answer as a correct answer when the first selection input is an input of selecting the first button; or an operation of determining an answer as an incorrect answer when the first selection input is an input of selecting any one of the at least one second button.

In accordance with some embodiments of the present disclosure, the test result data may include at least one of information on a total time required to perform the first task a preset first number of times, information on a number of times determined as a correct answer through the second sub-task, information on a number of times determined as an incorrect answer through the second sub-task, and information on response time taken from performing the first sub-task until receiving the first selection input.

In accordance with some embodiments of the present disclosure, the second task may include: a third sub-task that causes a test device of a test user to display a third button comprising a first equation and a fourth button comprising a second equation when a fifth button comprising a preset text to be displayed between the third button and the fourth button; and a fourth sub-task for determining whether an answer is correct according to a second selection input of selecting any one of the third button, the fourth button, and the fifth button.

In accordance with some embodiments of the present disclosure, the second task may perform the third sub-task and the fourth sub-task a preset second number of times while changing the first equation and the second equation.

In accordance with some embodiments of the present disclosure, the fourth sub-task may perform an operation of determining whether the second selection input is a correct answer based on a comparison result of a result value of the first equation and a result value of the second equation.

In accordance with some embodiments of the present disclosure, the test result data may include at least one of information on a total time required to perform the second task a preset second number of times, information on the number of times determined as a correct answer through the fourth sub-task, information on the number of times determined as an incorrect answer through the fourth sub-task, and information on response time taken from performing the third sub-task until receiving the second selection input.

In accordance with some embodiments of the present disclosure, the third task may include: a fifth sub-task that causes a test device of a test user to display at least two objects for a preset time; a sixth sub-task that causes the test device to display a first object of the at least two objects on a third region and to display a second object of the at least two objects and at least one additional object different from the at least two objects on a fourth region; and a seventh sub-task that determines whether an answer is correct according to a third selection input of selecting any one from among a plural objects displayed on the fourth region.

In accordance with some embodiments of the present disclosure, the seventh sub-task may further include an operation of deactivating selection inputs for the plural objects as receiving the third selection input.

In accordance with some embodiments of the present disclosure, the seventh sub-task may include: an operation of determining an answer as a correct answer when the third selection input is an input of selecting the second object; or an operation of determining an answer as an incorrect when the third selection input is an input of selecting any one of the at least one additional object.

In accordance with some embodiments of the present disclosure, the third task may perform the fifth sub-task, the sixth sub-task, and the seventh sub-task a preset third number of times while changing the at least two objects and the at least one additional object.

In accordance with some embodiments of the present disclosure, the test result data may include at least one of information on a total time required to perform the third task the preset third number of times, information on a number of times determined as a correct answer through the seventh sub-task, information on a number of times determined as an incorrect answer through the seventh sub-task, and information on response time taken from performing the sixth sub-task until receiving the third selection input.

In accordance with another aspect of the present invention, there is provided a computer program stored on a computer-readable storage medium, wherein the computer program performs steps of training a dementia identification model when executed by at least one processor of a device, the steps include: obtaining test result data through at least one of a first task related to Stroop test, a second task related to a computational power test, and a third task related to a memory test; and labeling the test result data with a score value to train the dementia identification model.

In accordance with yet another aspect of the present invention, there is provided a device for training a dementia identification model, the device includes: a storage configured to store at least one program command; and at least one processor configured to perform the at least one program command, wherein the at least one processor obtains test result data through at least one of a first task related to Stroop test, a second task related to a computational power test, and a third task related to a memory test, and labels the test result data with a score value to train the dementia identification model.

It will be understood that technical solutions of the present disclosure are not limited to the aforementioned solutions and other technical solutions not referred to herein will be clearly understood by those skilled in the art from the description below.

Advantageous Effects

The effect of a technique for training a dementia identification model according to the present disclosure is as follows.

By using a dementia identification model trained according to some embodiments of the present disclosure, dementia can be accurately diagnosed by a method where patients hardly feel rejection.

It will be understood that effects obtained by the present disclosure are not limited to the aforementioned effect and other effects not referred to herein will be clearly understood by those skilled in the art from the description below.

BRIEF DESCRIPTION OF DRAWINGS

Various embodiments of the present disclosure are described with reference to the accompanying drawings. Here, like reference numbers are used to refer to like elements. In the following embodiments, numerous specific details are set forth so as to provide a thorough understanding of one or more embodiments for purposes of explanation. It will be apparent, however, that such embodiment (s) may be practiced without these specific details.

DETAILED DESCRIPTION

Figure 1:
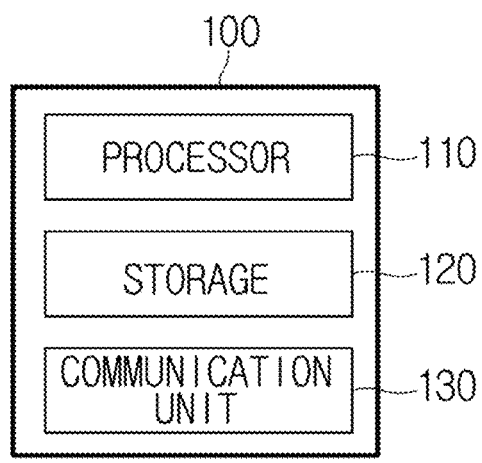
FIG. 1 is a block diagram illustrating a device for training a dementia identification model according to some embodiments of the present disclosure.

Hereinafter, various embodiments of an apparatus according to the present disclosure and a method of controlling the same will be described in detail with reference to the accompanying drawings. Regardless of the reference numerals, the same or similar components are assigned the same reference numerals, and overlapping descriptions thereof will be omitted.

Objectives and effects of the present disclosure, and technical configurations for achieving the objectives and the effects will become apparent with reference to embodiments described below in detail in conjunction with the accompanying drawings. In describing one or more embodiments of the present disclosure, a detailed description of known functions and configurations incorporated herein will be omitted when it may make the subject matter of the present disclosure unclear.

The terms used in the specification are defined in consideration of functions used in the present disclosure, and can be changed according to the intent or conventionally used methods of clients, operators, and users. The features of the present disclosure will be more clearly understood from the accompanying drawings and should not be limited by the accompanying drawings, and it is to be appreciated that all changes, equivalents, and substitutes that do not depart from the spirit and technical scope of the present disclosure are encompassed in the present disclosure.

The suffixes "module" and "unit" of elements herein are used for convenience of description and thus can be used interchangeably and do not have any distinguishable meanings or functions.

Terms including an ordinal number, such as first, second, etc., may be used to describe various elements, but the elements are not limited by the terms. The above terms are used only for the purpose of distinguishing one component from another component. Therefore, a first component mentioned below may be a second component within the spirit of the present description.

A singular expression includes a plural expression unless the context clearly dictates otherwise. That is, a singular expression in the present disclosure and in the claims should generally be construed to mean "one or more" unless specified otherwise or if it is not clear from the context to refer to a singular form.

The terms such as "include" or "comprise" may be construed to denote a certain characteristic, number, step, operation, constituent element, or a combination thereof, but may not be construed to exclude the existence of or a possibility of addition of one or more other characteristics, numbers, steps, operations, constituent elements, or combinations thereof.

The term "or" in the present disclosure should be understood as "or" in an implicit sense and not "or" in an exclusive sense. That is, unless otherwise specified or clear from context, "X employs A or B" is intended to mean one of natural implicit substitutions. That is, when X employs A; when X employs B; or when X employs both A and B, "X employs A or B" can be applied to any one of these cases. Furthermore, the term "and/or" as used in the present disclosure should be understood to refer to and encompass all possible combinations of one or more of listed related items.

As used in the present disclosure, the terms "information" and "data" may be used interchangeably.

Unless otherwise defined, all terms (including technical and scientific terms) used in the present disclosure may be used with meanings that can be commonly understood by those of ordinary skill in the technical field of the present disclosure. Also, terms defined in general used dictionary are not to be excessively interpreted unless specifically defined However, the present disclosure is not limited to embodiments disclosed below and may be implemented in various different forms. Some embodiments of the present disclosure are provided merely to fully inform those of ordinary skill in the technical field of the present disclosure of the scope of the present disclosure, and the present disclosure is only defined by the scope of the claims. Therefore, the definition should be made based on the content throughout the present disclosure.

In accordance with some embodiments of the present disclosure, at least one processor (hereinafter referred to as a 'processor') of a device may train a dementia identification model. Specifically, the processor of the device of the present disclosure may obtain test result data through at least one of the first task related to the Stroop test, the second task related to a computational power test, and the third task related to a memory test and may use the obtained data as input data for training. In addition, the score value may be used as labeling data. The processor may train the dementia identification model using input data for training and labeling data. As described above, the accuracy of the dementia identification model may be improved by training the dementia identification model. Hereinafter, the method of training the dementia identification model is described in detail with reference to FIGS. 1 to 5.

FIG. 1 is a block diagram illustrating a device for training a dementia identification model according to some embodiments of the present disclosure.

Referring to FIG. 1, a device 100 for training a dementia identification model may include a processor 110, a storage 120, and a communication unit 130. The components shown in FIG. 1 are not essential in implementing the device 100, and thus, the device 100 described in the present disclosure may have more or fewer components than those listed above.

Each component of the device 100 of the present disclosure may be integrated, added, or omitted according to the specifications of the device 100 that is actually implemented. That is, as needed, two or more components may be combined into one component or one component may be subdivided into two or more components. In addition, a function performed in each block is for explaining an embodiment of the present disclosure, and the specific operation or device does not limit the scope of the present disclosure.

The device 100 described in the present disclosure may include any device that transmits and receives at least one of data, content, service, and application, but the present disclosure is not limited thereto.

The device 100 of the present disclosure may be paired with or connected to another device, an external server, etc. through a wire/wireless network, and predetermined data may be transmitted/received through the device 100. In this case, data transmitted/received through the device 100 may be converted before transmission/reception.

The device 100 of the present disclosure includes, for example, any standing devices such as a server, a personal computer (PC), a microprocessor, a mainframe computer, a digital processor and a device controller; and any mobile devices (or handheld device) such as a smart phone, a tablet PC, and a notebook, but the present disclosure is not limited thereto.

In the present disclosure, the term "server" refers to a device or system that supplies data to or receives data from various types of user terminals, i.e., a client. For example, a web server or portal server that provides a web page or a web content (or a web service), an advertising server that provides advertising data, a content server that provides content, an SNS server that provides a Social Network Service (SNS), a service server provided by a manufacturer, a Multichannel Video Programming Distributor (MVPD) that provides Video on Demand (VoD) or a streaming service, a service server that provides a pay service, or the like may be included as a server.

In the present disclosure, the device 100 means a server according to context, but may mean a fixed device or a mobile device, or may be used in an all-inclusive sense unless specified otherwise.

The processor 110 may generally control the overall operation of the device 100 in addition to an operation related to an application program. The processor 110 may provide or process appropriate information or functions by processing signals, data, information, etc. that are input or output through the components of the device 100 or driving an application program stored in the storage 120.

The processor 110 may control at least some of the components of the device 100 to drive an application program stored in the storage 120. Furthermore, the processor 110 may operate by combining at least two or more of the components included in the device 100 to drive the application program.

The processor 110 may include one or more cores, and may be any of a variety of commercial processors. For example, the processor 110 may include a Central Processing Unit (CPU), General Purpose Graphics Processing Unit (GPUGP), Tensor Processing Unit (TPU), and the like of the device. However, the present disclosure is not limited thereto.

The processor 110 of the present disclosure may be configured as a dual processor or other multiprocessor architecture. However, the present disclosure is not limited thereto.

The processor 110 may perform data processing for training a dementia identification model according to some embodiments of the present disclosure by reading a computer program stored in the storage 120.

According to some embodiments of the present disclosure, the processor 110 may perform an operation for training the neural network. Here, the training may mean a process of determining the weight factor of a neural network by a method of updating the weight factor of a neural network by back-propagating a difference value (error) between label data labeled in input data for training and prediction data output from the dementia identification model.

At least one of CPU, GPGPU, and TPU of the processor 110 may process training of a network function. For example, CPU and GPGPU may process training of a network function and data classification using the network function.

The dementia identification model in the present disclosure may be composed of a set of interconnected computational units, which may generally be referred to as nodes. These nodes may also be referred to as neurons. The dementia identification model may be configured to include at least one node. Nodes (or neurons) constituting the dementia identification model may be interconnected by one or more links.

In the dementia identification model, one or more nodes connected through a link may relatively form a relationship between an input node and an output node. The concepts of an input node and an output node are relative, and any node in an output node relationship with respect to one node may be in an input node relationship in a relationship with another node, and vice versa. As described above, an input node-to-output node relationship may be created around a link. One output node may be connected to one input node through a link, and vice versa.

In the relation between the input node and the output node connected through one link, a value of data of the output node may be determined based on data that is input to the input node. Here, the link interconnecting the input node and the output node may have a weight. The weight may be variable, and may be changed by a user or an algorithm so as for the neural network to perform a desired function.

For example, when one or more input nodes are connected to one output node by each link, the output node may determine an output node value based on values that are input to input nodes connected to the output node and based on a weight set in a link corresponding to each input node.

As described above, in the dementia identification model, one or more nodes may be interconnected through one or more links to form an input node and output node relationship in the neural network. The characteristics of the dementia identification model may be determined according to the number of nodes and links in the dementia identification model, a correlation between nodes and links, and a weight value assigned to each of the links.

The dementia identification model may consist of a set of one or more nodes. A subset of nodes constituting the dementia identification model may constitute a layer. Some of the nodes constituting the dementia identification model may configure one layer based on distances from an initial input node. For example, a set of nodes having a distance of n from the initial input node may constitute n layers. The distance from the initial input node may be defined by the minimum number of links that should be traversed to reach the corresponding node from the initial input node. However, the definition of such a layer is arbitrary for the purpose of explanation, and the order of the layer in the dementia identification model may be defined in a different way from that described above. For example, a layer of nodes may be defined by a distance from a final output node.

The initial input node may refer to one or more nodes to which data (test result data) is directly input without going through a link in a relationship with other nodes among nodes in the dementia identification model. Alternatively, in a relationship between nodes based on a link in the dementia identification model, the initial input node may mean nodes that do not have other input nodes connected by a link. Similarly, the final output node may refer to one or more nodes that do not have an output node in relation to other nodes among nodes in the dementia identification model. In addition, a hidden node may refer to nodes constituting the dementia identification model other than the first input node and the last output node.

In the dementia identification model according to some embodiments of the present disclosure, the number of nodes in the input layer may be greater than the number of nodes in the output layer, and the neural network may have a form wherein the number of nodes decreases as it progresses from the input layer to the hidden layer. However, the present disclosure is not limited thereto.

According to some embodiments of the present disclosure, the dementia identification model may have a deep neural network structure.

A Deep Neural Network (DNN) may refer to a neural network including a plurality of hidden layers in addition to an input layer and an output layer. DNN may be used to identify the latent structures of data.

DNN may include convolutional neural networks (CNNs), Recurrent Neural Networks (RNNs), auto encoders, Generative Adversarial Networks (GANs), and a Restricted Boltzmann Machines (RBM), a Deep Belief Network (DBN), a Q network, a U network, a Siamese network, a Generative Adversarial Network (GAN), and the like. These DNNs are only provided as examples, and the present disclosure is not limited thereto.

The dementia identification model of the present disclosure may be learned in a supervised learning manner. However, the present disclosure is not limited thereto, and the dementia identification model may be learned in at least one manner of unsupervised learning, semi supervised learning, or reinforcement learning.

Learning of the dementia identification model may be a process of applying knowledge for a neural network to perform a specific operation to the neural network.

The dementia identification model may be trained in a way that minimizes errors in output. Learning of the dementia identification model is a process of repeatedly inputting learning data (test result data for learning) into the dementia identification model, calculating errors of an output (score value predicted through the neural network) and target (score value used as label data) of the dementia identification model on the learning data, and updating the weight of each node of the dementia identification model by back-propagating the error of the dementia identification model from an output layer of the dementia identification model to an input layer in a direction of reducing the error.

A change amount of a connection weight of each node to be updated may be determined according to a learning rate. Calculation of the dementia identification model on the input data and backpropagation of errors may constitute a learning cycle (epoch). The learning rate may be differently applied depending on the number of repetitions of a learning cycle of the dementia identification model. For example, in an early stage of learning the dementia identification model, a high learning rate may be used to enable the dementia identification model to quickly acquire a certain level of performance, thereby increasing efficiency, and, in a late stage of learning the dementia identification model, accuracy may be increased by using a low learning rate.

In the learning of the dementia identification model, the learning data may be a subset of actual data (i.e., data to be processed using the learned dementia identification model), and thus, there may be a learning cycle wherein errors for learning data decrease but errors for real data increase. Overfitting is a phenomenon wherein errors on actual data increase due to over-learning on learning data as described above.

Overfitting may act as a cause of increasing errors in a machine learning algorithm. To prevent such overfitting, methods such as increasing training data; regularization; and dropout that deactivate some of nodes in a network during a learning process, and utilization of a batch normalization layer may be applied.

The storage 120 may store data supporting various functions of the device 100. The storage 120 may store a plurality of application programs (or applications) driven in the device 100, and data, commands, and at least one program command for the operation of the device 100. At least some of these application programs may be downloaded from an external server through wireless communication. In addition, at least some of these application programs may exist in the device 100 from the time of shipment for basic functions of the device 100. Meanwhile, the application program may be stored in the storage 120, installed in the device 100, and driven by the processor 110 to perform the operation (or function) of the device 100.

The storage 120 may store any type of information generated or determined by the processor 110 and any type of information received through the communication unit 130.

The storage 120 may include at least one type of storage medium of a flash memory type, a hard disk type, a Solid State Disk (SSD) type, a Silicon Disk Drive (SDD) type, a multimedia card micro type, a card-type memory (e.g., SD memory, XD memory, etc.), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. The device 100 may be operated in relation to a web storage that performs a storage function of the storage 120 on the Internet.

The communication unit 130 may include one or more modules that enable wire/wireless communication between the device 100 and a wire/wireless communication system, between the device 100 and another device, or between the device 100 and an external server. In addition, the communication unit 130 may include one or more modules that connect the device 100 to one or more networks.

The communication unit 130 refers to a module for wired/wireless Internet connection, and may be built-in or external to the device 100. The communication unit 130 may be configured to transmit and receive wire/wireless signals.

The communication unit 130 may transmit/receive a radio signal with at least one of a base station, an external terminal, and a server on a mobile communication network constructed according to technical standards or communication methods for mobile communication (e.g., Global System for Mobile communication (GSM), Code Division Multi Access (CDMA), Code Division Multi Access 2000 (CDMA2000), Enhanced Voice-Data Optimized or Enhanced Voice-Data Only (EV-DO), Wideband CDMA (WCDMA), High Speed Downlink Packet Access (HSDPA), High Speed Uplink Packet Access (HSUPA), Long Term Evolution (LTE), Long Term Evolution-Advanced (LTE-A), etc.).

An example of wireless Internet technology includes Wireless LAN (WLAN), Wireless-Fidelity (Wi-Fi), Wireless Fidelity (Wi-Fi) Direct, Digital Living Network Alliance (DLNA), Wireless Broadband (WiBro), World Interoperability for Microwave Access (WiMAX), High Speed Downlink Packet Access (HSDPA), High Speed Uplink Packet Access (HSUPA), Long Term Evolution (LTE), Long Term Evolution-Advanced (LTE-A), and the like. However, in a range including Internet technologies not listed above, the communication unit 130 may transmit/receive data according to at least one wireless Internet technology.

In addition, the communication unit 130 may be configured to transmit and receive signals through short range communication. The communication unit 130 may perform short range communication using at least one of Bluetooth™, Radio Frequency Identification (RFID), Infrared Data Association (IrDA), Ultra-Wideband (UWB), ZigBee, Near Field Communication (NFC), Wireless-Fidelity (Wi-Fi), Wi-Fi Direct and Wireless Universal Serial Bus (Wireless USB) technology. The communication unit 130 may support wireless communication through short range communication networks (wireless area networks). The short range communication networks may be wireless personal area networks.

The device 100 according to some embodiments of the present disclosure may be connected to the test device 200 and the wire/wireless network 300 through the communication unit 130.

In the present disclosure, the test device may refer to a device where various test users perform tests to secure input data for training the dementia identification model. Here, the test device may be any mobile devices (or handheld device) such as a smart phone, a tablet PC, and a notebook, but the present disclosure is not limited thereto.

The test users may include a user classified as a patient with mild cognitive impairment, a user classified as an Alzheimer's patient, a user classified as normal, and the like. However, the present disclosure is not limited thereto.

The test device of the present disclosure may include a processor, a storage, a communication unit, a display and a sound output unit. However, these components are not essential in implementing the test device, and thus, the test device described in the present disclosure may have more or fewer components than those listed above.

Since the processor, storage and communication unit of the test device are the same as the processor 110, storage 120 and communication unit 130 of the device 100, a duplicate description will be omitted, and differences therebetween will be mainly described below.

Since high processing speed and computational power are required to perform an operation using the dementia identification model, the dementia identification model may be stored only in the storage 120 of the device 100 and may not be stored in the storage of the test device. Therefore, a dementia identification model may be trained in a state of being stored in the storage 120 of the device 100.

Meanwhile, when training of the dementia identification model is completed, it is possible to identify whether dementia is present using the dementia identification model. For example, the processor 110 of the device 100 may receive test result data from a user terminal of a user who needs to identify whether dementia is present, input the test result data into the dementia identification model to identify whether dementia is present, followed by transmitting the result to the user terminal. That is, in the present disclosure, test result data may be used as a digital biomarker (a biomarker acquired through a digital device).

The display may display (output) information processed by the test device 200. For example, the display may display execution screen information of an application program driven in the test device 200, or User Interface (UI) and Graphic User Interface (GUI) information according to the execution screen information.

The display may include at least one of a Liquid Crystal Display (LCD), a Thin-Film Transistor-Liquid Crystal Display (TFT LCD), an Organic Light-Emitting Diode (OLED), a flexible display, a 3(d) display, an e-ink display. However, the present disclosure is not limited thereto.

The display may include a touch sensor for detecting a touch on the display so as to receive a control command input by a touch method. The display may implement a touch screen by forming a layered structure with the touch sensor or being integrally formed therewith. Such a touch screen may function as a user input unit providing an input interface between the test device and the user and, at the same time, may provide an output interface between the test device and the user.

The touch sensor may detect a touch (or a touch input or a selection input) applied to the display using at least one of various touch methods such as a resistive film method, a capacitive method, an infrared method, an ultrasonic method, and a magnetic field method.

For example, the touch sensor may be configured to convert a change in pressure applied to a specific part of the touch screen or a change in capacitance occurring in a specific part of the touch screen into an electrical input signal. The touch sensor may be configured to detect a position and area touched on the touch sensor by a touch object applying a touch on the touch screen, a pressure at the time of the touch, an capacitance at the time of the touch, etc.

Here, the touch object is an object that applies a touch to the touch sensor, and may be, for example, a finger, a touch pen, a stylus pen, a pointer, or the like.

As such, when there is a touch input (or selection input) to the touch sensor, a signal(s) corresponding thereto is sent to a touch controller. The touch controller processes the signal(s) and then sends corresponding data to the processor. Accordingly, the processor may know which area of the display has been touched, and the like. Here, the touch controller may be a component separate from the processor or may be the processor itself.

In accordance with some embodiments of the present disclosure, the display may display an execution screen of at least one of the Stroop test, a computational power test and a memory test. In addition, a button or object displayed on the execution screen may be selected through a touch input of a test user.

The sound output unit of the test device may output audio data (or sound data, etc.) received from the communication unit or stored in the storage. The sound output unit may output a sound signal related to a function performed by the test device.

The sound output unit may include a receiver, a speaker, a buzzer, and the like. That is, the sound output unit may be implemented as a receiver or may be implemented in the form of a loudspeaker. However, the present disclosure is not limited thereto.

Hereinafter, the method of training the dementia identification model is described in detail with reference to FIG. 2.

Figure 2:
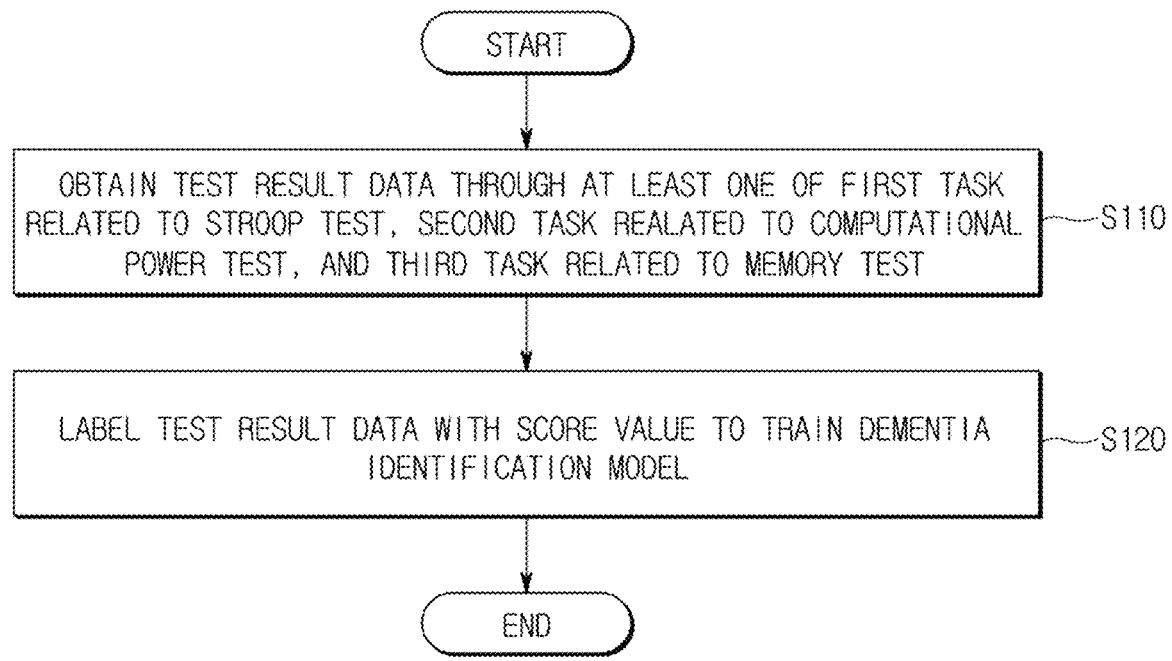
FIG. 2 is a flowchart illustrating an example of a method of training the dementia identification model according to some embodiments of the present disclosure.

FIG. 2 is a flowchart illustrating an example of a method of training the dementia identification model according to some embodiments of the present disclosure. In describing FIG. 2, the above-described particulars with reference to FIG. 1 will not be described again, and differences will be mainly described below.

Referring to FIG. 2, the processor 110 may obtain test result data through at least one of the first task related to the Stroop test, the second task related to a computational power test, and the third task related to a memory test (S110).

Specifically, in step S110, when the device 100 receives a command to execute at least one of the Stroop test, a computational power test and a memory test from the test device, the processor 110 of the device 100 may cause at least one of the Stroop test, the computational power test and the memory test to proceed in the test device. In this case, a test user may proceed with the test through the test device. In addition, the test device may transmit test result data, obtained by performing the test, to the device 100. The processor 110 of the device 100 may control the communication unit 130 to obtain test result data obtained through at least one of the first task related to the Stroop test, the second task related to a computational power test, and the third task related to a memory test. Here, the test result data may include one or more result data obtained through the at least one test.

The Stroop test may refer to the effect that the reaction time for a given task varies according to attention, or a test conducted using such a phenomenon. The computational power test may mean a test performed in a manner of providing an equation and selecting a correct answer according to the equation. The memory test may refer to a test performed in a manner of memorizing a plurality of objects displayed on a previous screen and selecting the plurality of objects from a currently displayed screen. However, the present disclosure is not limited thereto, and the Stroop test, the computational power test, and the memory test may be performed through various methods.

When the test result data is obtained in step S110, the processor 110 may label the test result data with a score value to train the dementia identification model. Here, the score value may have a correlation with a score (hereinafter referred to as a paper score) obtained after a test user performs at least one of the Stroop test, a computational power test, and a memory test through paper. For example, the score value of a test user recognized as dementia due to a low paper score may be assigned a high value, and the score value of a test user recognized as not having dementia due to a high paper score may be assigned a low value, but the present disclosure is not limited thereto.

As a result, test result data obtained by various test users executing at least one of the Stroop test, a computational power test, and a memory test through the test device may be labeled with a score value having a correlation with the paper score.

In addition, the processor 110 may train the dementia identification model using the test result data and the score values labeled therewith. However, the present disclosure is not limited thereto.

In accordance with some embodiments of the present disclosure, a user in need of dementia identification may execute at least one of the Stroop test, a computational power test, and a memory test using his/her user terminal. In addition, the device 100 may obtain test result data generated by executing at least one test in the user terminal, and then input the data into a pre-trained dementia identification model to obtain a score value. In addition, the processor 110 may determine whether dementia is present, based on the magnitude of the score value, but the present disclosure is not limited thereto.

Meanwhile, a user terminal of a user requiring dementia identification may be a mobile terminal like the test terminal. That is, it is possible to train the dementia identification model by securing input data for training through the mobile terminal. In addition, it is possible to identify whether dementia is present, by inputting the input data obtained through the mobile terminal into the pre-trained dementia identification model. As described above, since training is performed with data obtained using the same type of terminal as well as inference is made, the accuracy of dementia identification of the pre-trained dementia identification model may be improved.

When determining whether dementia is present according to some embodiments described above, dementia may be accurately diagnosed in a method in which a patient hardly feels rejection.

In accordance with some embodiments of the present disclosure, the processor 110 may obtain test result data through a first task related to the Stroop test. Here, the first task may include a first sub-task that causes a test device of a test user to display a first number of numeric texts in a first region while interworking with displaying a first button for displaying a first numeral indicating the first number on a second region; and at least one second button for displaying a number different from the first number; and a second sub-task that determines whether an answer is correct according to a first selection input of selecting any one of the first button and the at least one second button. Hereinafter, a detailed description is provided with reference to FIG. 3.

Figure 3:
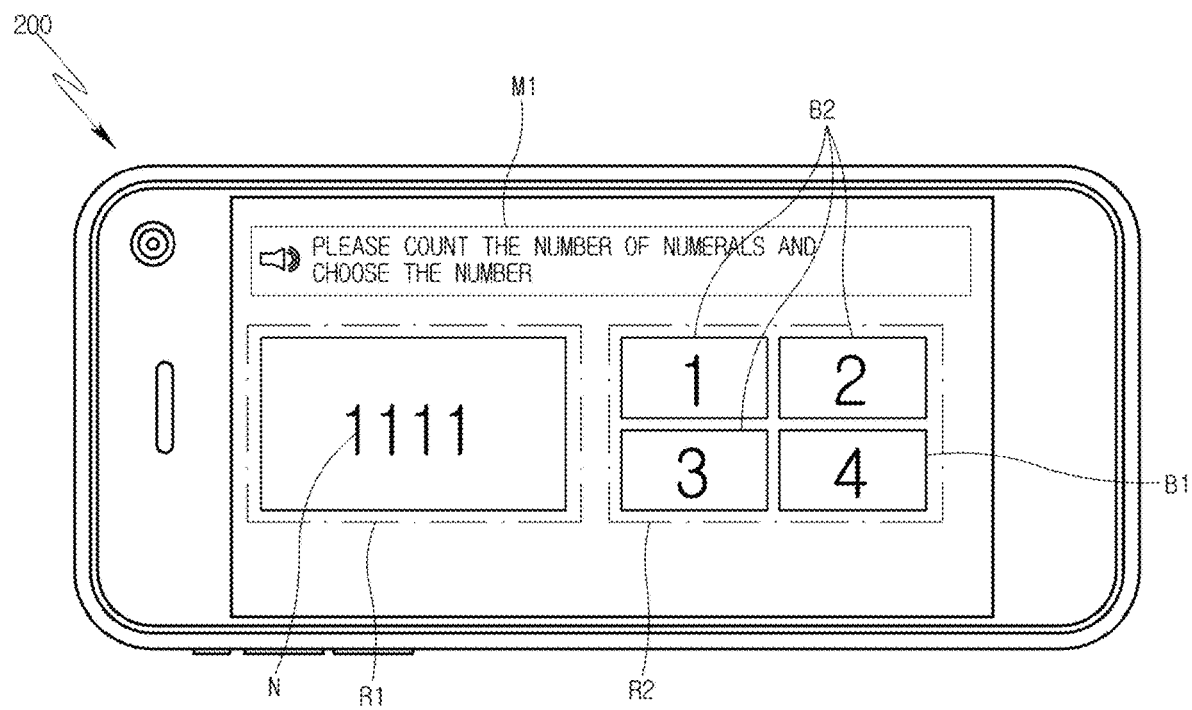
FIG. 3 is a diagram illustrating an example of a method of performing a first task related to the Stroop test according to some embodiments of the present disclosure.

FIG. 3 is a diagram illustrating an example of a method of performing a first task related to the Stroop test according to some embodiments of the present disclosure. In describing FIG. 3, the contents provided above with reference to FIGS. 1 and 2 will not be described again, and differences will be mainly described below.

Referring to FIG. 3, when the Stroop test is executed in a test device 200, a screen related to the Stroop test may be displayed on a screen of the test device 200.

Specifically, when a test user of the test device 200 executes the Stroop test, the test device 200 may transmit a signal related to the execution of the Stroop test to the device 100. When the device 100 receives the signal related to the execution of the Stroop test, the device 100 may perform a first sub-task causing a screen related to the Stroop test to be displayed on the test device 200.

For example, the processor 110 of the device 100 may cause the test device 200 of the test user to display the first number (e.g., four) of numeric text (e.g., "1") in a first region (R1) while interworking with displaying a first button B1, on which a first numeral (e.g., "4") indicating a first number is displayed; and second buttons, on which second numerals (e.g., "1", "2", "3") different from the first number are displayed, in a second region R2. Here, the first region R1 may be a left region on the screen, and the second region R2 may be a right region on the screen, but the present disclosure is not limited thereto.

In accordance with some embodiments of the present disclosure, when a screen related to the Stroop test is displayed on the test device 200, a message M1 related to the test content may be displayed in an arbitrary area. Here, the test user may recognize through the message M1 what the given task is. In addition, the test device 200 may output a sound (e.g., a voice explaining what is contained in message M1) related to the message M1 through the sound output unit while interworking with displaying the message M1 on the screen through the display. As described above, when the test user is recognized by a sound along with the message M1 of what a given task is, the possibility that the test user will select an incorrect answer by mistake may be reduced.

Meanwhile, the processor 110 may perform a second sub-task of determining whether an answer is correct according to a first selection input of selecting any one of the first button B1 and the at least one second button B2.

Specifically, when the first selection input of selecting any one of the first button B1 and the at least one second button B2 is detected in the test device 200, the test device 200 may transmit information (e.g., information on which button is selected) on the first selection input to the device 100. In this case, the device 100 may determine whether the answer is correct based on the received information.

For example, the processor 110 of the device 100 may determine the answer as a correct answer when the first selection input is recognized as an input of selecting the first button B1, and may determine the answer as an incorrect answer when the first selection input is recognized as an input of selecting the at least one second button B2. That is, the second sub-task may include an operation of determining the answer as a correct answer when the first selection input is an input of selecting the first button or an operation of determining the answer as an incorrect when the first selection input is an input of selecting any one of the at least one second button.

In accordance with some embodiments of the present disclosure, the first task related to the Stroop test may perform the above-described first sub-task and second sub-task a preset first number of times while changing the first number of numeric texts and the numeric texts (N).

For example, when the first number of times is 2, the test device 200 may display four numeric texts (e.g., "1") in the first area R1, and the processor 110 of the device 100 may determine whether the answer is correct according to the first selection input. Next, the test device 200 may display three different numeric texts (e.g., 2) in the first area R1, and the processor 110 of the device 100 may determine again whether the answer is correct according to the first selection input. In this manner, the first sub-task and the second sub-task may be performed twice. The above-described example is merely an example, and the present disclosure is not limited thereto.

The Stroop test presented in FIG. 3 is to select the number of numeric texts presented in the first region R1. However, the present disclosure is not limited thereto, and in the Stroop test, selecting the same numeric texts as numeric texts presented in the first region R1 may be presented as a task. In this case, the processor 110 of the device 100 may determine the answer as a correct answer when the first selection input is recognized as a selection button of selecting a button displaying the same numeric text as the numeric text displayed in the first region R1 of the test device 200, and may determine the answer as an incorrect answer when the first selection input is recognized as a selection input of selecting a button displaying a numeric text different from the numeric text displayed in the first region R1.

In accordance with some embodiments of the present disclosure, the processor 110 may perform a first preliminary task such that the test user may check a test related to the first task before performing the first task. Here, since the first preliminary task is performed in the same manner as the above-described first task, a detailed description thereof will be omitted.

The test result data obtained in the first preliminary task may not be used when training the dementia identification model, and only the test result data obtained in the first task may be used when training the dementia identification model. However, to increase the accuracy of the dementia identification of the dementia identification model, the test result data obtained in the first preliminary task may also be used when training the dementia identification model.

Meanwhile, the test result data obtained through the above-described first task may include at least one of information on a total time required to perform the first task a preset first number of times, information on the number of times determined as a correct answer through the second sub-task, information on the number of times determined as an incorrect answer through the second sub-task, and information on response time taken from performing the first sub-task until receiving the first selection input. However, to improve the accuracy of dementia identification of the dementia identification model, all of the total time information, the information on the number of times determined as a correct answer, the information on the number of times determined as an incorrect answer and the response time information may be included in the test result data.

In accordance with some embodiments of the present disclosure, a user in need of dementia identification may execute the Stroop test using his/her user terminal. In addition, the device 100 may obtain test result data generated by executing the Stroop test in the user terminal, and then input the data into a pre-trained dementia identification model to obtain a score value. In addition, the processor 110 may determine whether dementia is present, based on the magnitude of the score value, but the present disclosure is not limited thereto.

In accordance with some embodiments of the present disclosure, the processor 110 may obtain the test result data through the second task related to a computational power test. Here, the second task may include a third sub-task that causes a test device of a test user to display a third button comprising a first equation and a fourth button comprising a second equation when a fifth button comprising a preset text to be displayed between the third button and the fourth button; and a fourth sub-task for determining whether an answer is correct according to a second selection input of selecting any one of the third button, the fourth button, and the fifth button. Hereinafter, a detailed description will be provided with reference to FIG. 4

Figure 4:
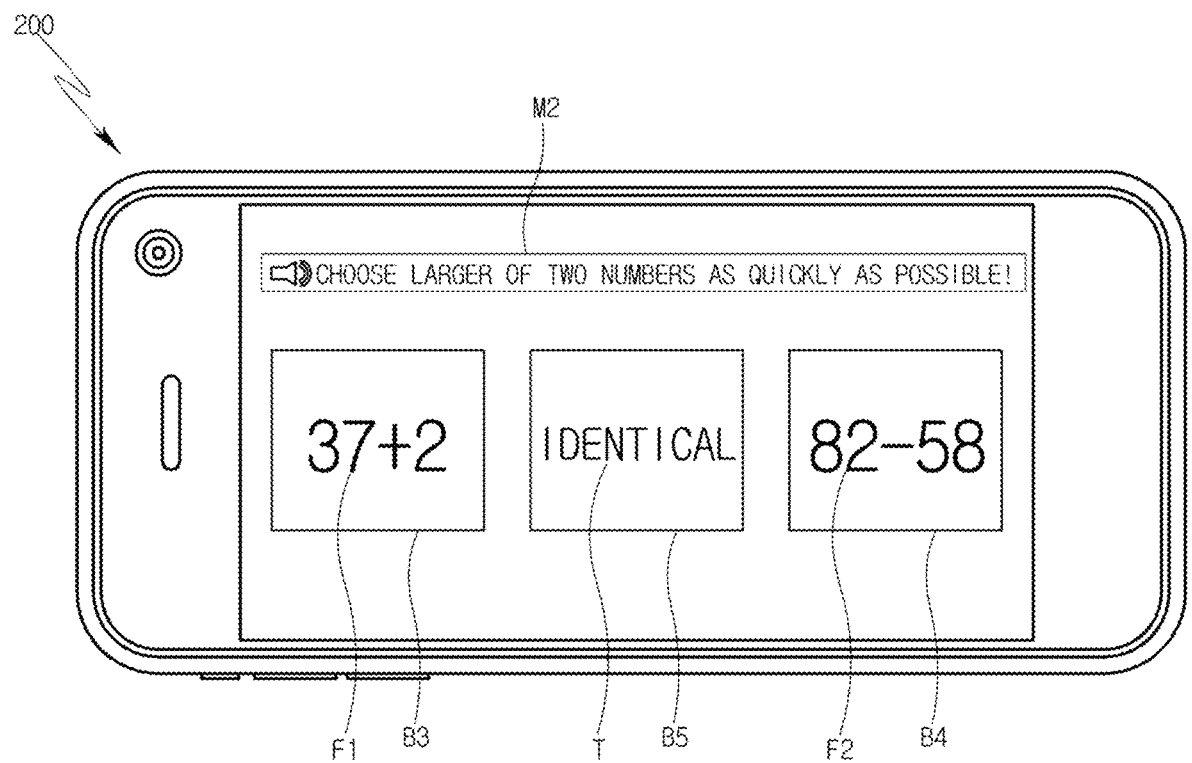
FIG. 4 is a diagram illustrating an example of a method of performing a second task related to a computational power test according to some embodiments of the present disclosure.

FIG. 4 is a diagram illustrating an example of a method of performing a second task related to a computational power test according to some embodiments of the present disclosure. In describing FIG. 4, the contents provided above with reference to FIGS. 1 and 2 will not be described again, and differences will be mainly described below.

Referring to FIG. 4, when a computational power test is executed in a test device 200, a screen related to the computational power test may be displayed on a screen of the test device 200.

Specifically, when a test user of the test device 200 executes the computational power test, the test device 200 may transmit a signal related to the execution of the computational power test to the device 100. When the device 100 receives the signal related to the execution of the computational power test, the device 100 may perform a third sub-task causing a screen related to the computational power test to be displayed on the test device 200.

For example, the processor 110 of the device 100 may perform the third sub-task causing the test device 200 of the test user to display the third button B3 including the first equation F1, the fourth button B4 including the second equation F2, and the fifth button B5 including the preset text T.

The fifth button B5 may be disposed between the third button B3 and the fourth button B4. When the fifth button B5 is disposed between the third button B3 and the fourth button B4, the possibility that the test user accidentally selects an incorrect answer may be reduced. However, the present disclosure is not limited thereto.

The preset text T may be a text indicating that the result value of the first equation F1 and the result value of the second equation F2 are the same. For example, the preset text T "identical" may be included in the fifth button B5. However, the present disclosure is not limited thereto.

The first equation F1 and the second equation F2 may include various types of equations. For example, the first equation F1 and the second equation F2 may be equations for adding, subtracting, multiplying, and dividing at least two numbers. However, the present disclosure is not limited thereto.

In accordance with some embodiments of the present disclosure, when a screen related to the computational power test is displayed on the test device 200, a message M2 related to the test content may be displayed in an arbitrary area. Here, the test user may recognize through the message M2 what the given task is. In addition, the test device 200 may output a sound (.g., a voice explaining what is contained in message M2) related to the message M2 through the sound output unit while interworking with displaying the message M2 on the screen through the display. As described above, when the test user is recognized by a sound along with the message M2 of what a given task is, the possibility that the test user will check an incorrect answer by mistake may be reduced.

Meanwhile, the processor 110 may perform a fourth sub-task of determining whether an answer is correct according to a second selection input of selecting any one of the third button B3, the fourth button B4, and the fifth button B5.

Specifically, when the second selection input of selecting any one of the third button B3, the fourth button B4, and the fifth button B5 is detected in the test device 200, the test device 200 may transmit information (e.g., information on which button is selected) on the second selection input to the device 100. In this case, the device 100 may determine whether the answer is correct based on the received information.

Specifically, the processor 110 of the device 100 may perform an operation of determining whether the second selection input is a correct answer, as the fourth sub-task, based on a comparison result of a result value of the first equation and a result value of the second equation.

When the result value of the first equation F1 is greater than the result value of the second equation F2 as shown in FIG. 4, the processor 110 may determine that the answer is correct when recognizing that the third button B3 is selected according to the second selection input. In addition, the processor 110 may determine that the answer is incorrect when recognizing that the fourth button B4 or the fifth button B5 is selected according to the second selection input.

The reason for determining the correct answer as described above is that the task presented in the memory test is to select a formula having a larger result value. Accordingly, if the task is changed, the correct answer may be changed. That is, if selecting a formula with a smaller result value is a task presented in the memory test, the correct answer may be changed.

In accordance with some embodiments of the present disclosure, the second task related to a computational power test may perform the third sub-task and the fourth sub-task a preset second number of times while changing the first equation F1 and the second equation F2.

In accordance with some embodiments of the present disclosure, the processor 110 may perform a second preliminary task such that the test user may check a test related to the second task before performing the second task. Here, since the second preliminary task is performed in the same manner as the above-described second task, a detailed description thereof will be omitted.

The test result data obtained through the second preliminary task may not be used when training the dementia identification model, and only the test result data obtained through the second task may be used when training the dementia identification model. However, to increase the accuracy of the dementia identification of the dementia identification model, the test result data obtained in the second preliminary task may also be used when training the dementia identification model.

Meanwhile, the test result data obtained through the above-described second task may include at least one of information on the total time required to perform the second task a preset second number of times, information on the number of times determined as a correct answer through the fourth sub-task, information on the number of times determined as an incorrect answer through the fourth sub-task, and information on response time taken from performing the third sub-task until receiving the second selection input. However, to improve the accuracy of the dementia identification model, all of the total time information, the information on the number of times determined as a correct answer, the information on the number of times determined as an incorrect answer and the response time information may be included in the test result data.

In accordance with some embodiments of the present disclosure, a user in need of dementia identification may execute the computational power test using his/her user terminal. In addition, the device 100 may obtain test result data generated by executing the computational power test in the user terminal, and then input the data into a pre-trained dementia identification model to obtain a score value. In addition, the processor 110 may determine whether dementia is present, based on the magnitude of the score value, but the present disclosure is not limited thereto.

In accordance with some embodiments of the present disclosure, the processor 110 may obtain the test result data through the third task related to a memory test. Here, the third task may include a fifth sub-task that causes the test device of the test user to display at least two objects for a preset time; a sixth sub-task that causes the test device to display a first object of the at least two objects on a third region and to display a second object of the at least two objects and at least one additional object different from the at least two objects on a fourth region; and a seventh sub-task that determines whether an answer is correct according to a third selection input of selecting any one from among the plural objects displayed on the fourth region. Hereinafter, a detailed description will be provided with reference to FIG. 5.

Figure 5:
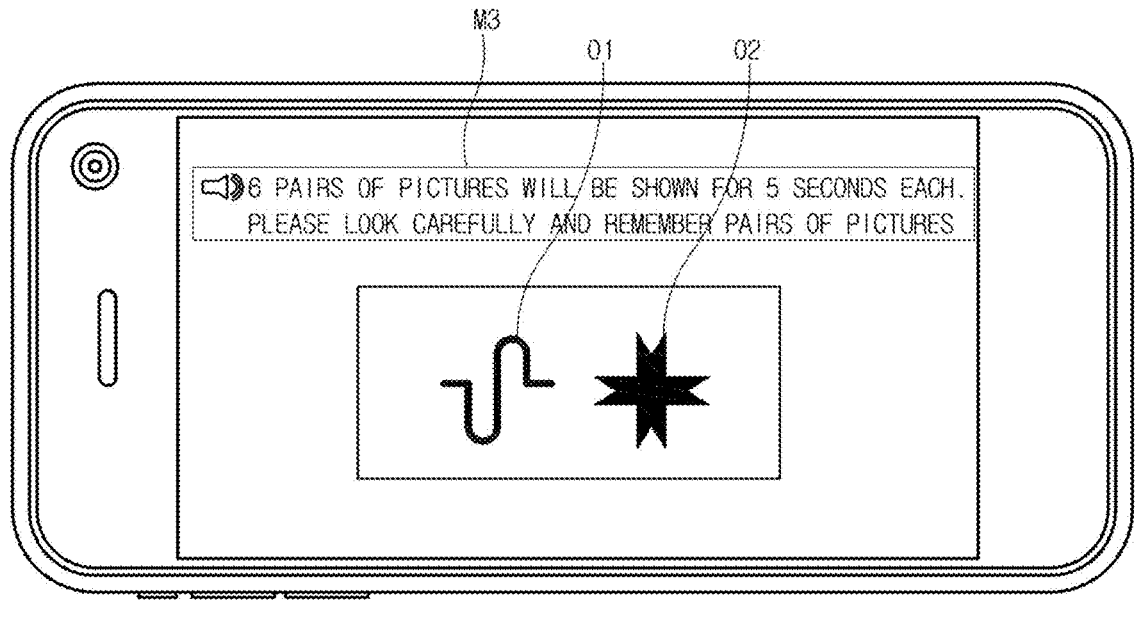
FIG. 5 is a diagram illustrating an example of a method of performing a third task related to a memory test according to some embodiments of the present disclosure.
Figure 5:
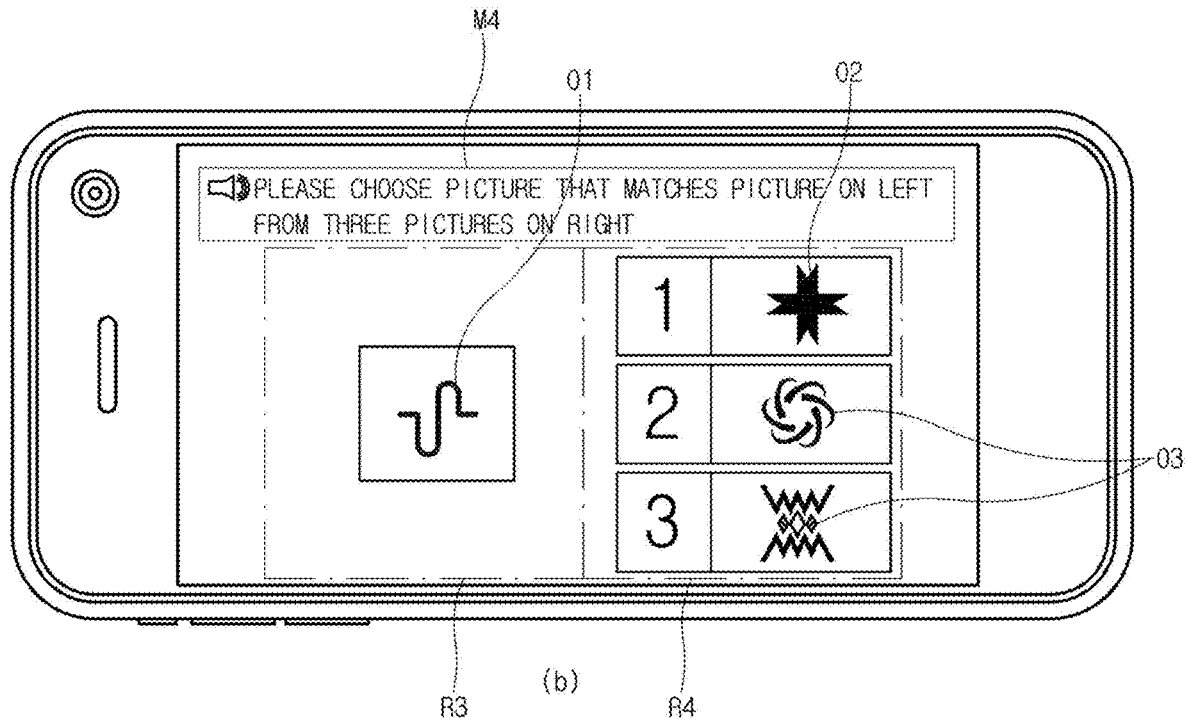

FIG. 5 is a diagram illustrating an example of a method of performing a third task related to a memory test according to some embodiments of the present disclosure. In describing FIG. 5, the contents provided above with reference to FIGS. 1 and 2 will not be described again, and differences will be mainly described below.

When the memory test is executed in the test device 200, a screen related to the memory test may be displayed on the screen of the test device 200.

Specifically, when the test user of the test device 200 executes the memory test, the test device 200 may transmit a signal, related to the execution of the memory test, to the device 100. When the device 100 receives a signal related to the execution of the memory test, the device 100 may perform the fifth sub-task and sixth sub-task causing a screen related to the memory test to be displayed on the test device 200.

For example, referring to FIG. 5(a), the processor 110 of the device 100 may perform the fifth sub-task causing the test device 200 of the test user to display at least two objects O1 and O2 for a preset time (e.g., 10 seconds). In addition, referring to FIG. 5(b), the processor 110 may perform the sixth sub-task that causes the test device 200 to display the first object O1 of the at least two objects on the third region R3 and to display the second object O2 of the at least two objects and at least one additional object O3 different from the at least two objects O1 and O2 on the fourth region R4. That is, when the preset time elapses after performing the fifth sub-task, the sixth sub-task may be performed.

Each of the at least two objects O1 and O2 of the present disclosure may have different forms and/or shapes. For example, the at least two objects may include a first object O1 having a first shape and a second object O2 having a second shape different from the first shape.

Each of the at least one additional object O3 of the present disclosure may have a form and/or shape different from each of the at least two objects O1 and O2. In addition, each of at least one additional object O3 may have a different form and/or shape.

The third region R3 may be located on the left side of the screen, and the fourth region R4 may be located on the right side of the screen. However, the present disclosure is not limited thereto.

Referring to FIG. 5(a) again, as the fifth sub-task is performed, a message M3 indicating a task to be performed by the test user may be displayed on a screen that is currently being displayed on the test device 200. For example, the message M3 may include content to memorize at least two objects O1 and O2 that are currently being displayed on the screen.

Referring to FIG. 5(b) again, as the sixth sub-task is performed, a message M4 indicating a task to be performed by the test user may be displayed on a screen that is currently being displayed on the test device 200. For example, the message M4 may include content to select the second object O2 included with the first object O1 displayed in the third region R3 on the screen displayed when the fifth sub-task is performed.

In addition, the test device 200 may output a sound (e.g., a voice explaining what is contained in messages M1 and M2) related to the messages M1 and M2 through the sound output unit while interworking with displaying the messages M1 and M2 on the screen through the display. As described above, when the test user is informed of a task that the test user needs to perform by sound together with the messages M3 and M4, the test user can clearly recognize what the task needs to be performed now.

Meanwhile, the processor 110 may perform a seventh sub-task of determining whether an answer is correct according to the third selection input of selecting any one of the plural objects O2 and O3 displayed on the fourth region R4.

Specifically, when the third selection input of selecting any one of the plural objects displayed on the fourth region R4 is detected, the test device 200 may transmit information (e.g., information on which object is selected) on the third selection input to the device 100. In this case, the device 100 may determine whether the answer is correct based on the received information.

For example, the processor 110 may determine the answer as a correct answer when the third selection input is recognized as an input of selecting the second object O2.

As another example, the processor 110 may determine the answer as an incorrect answer when the third selection input is recognized as an input of selecting any one of at least one additional object O3.

That is, the seventh sub-task may include an operation of determining an answer as a correct answer when the third selection input is an input of selecting the second object; or an operation of determining an answer as an incorrect when the third selection input is an input of selecting any one of the at least one additional object.

In accordance with some embodiments of the present disclosure, the third task related to the memory test may perform the fifth sub-task, the sixth sub-task, and the seventh sub-task a preset third number of times while changing the at least two objects O1 and O2 and the at least one additional object O3. Here, when changing the plural objects O1, O2, and O3, all of the plural objects O1, O2, and O3 or at least some of the plural objects O1, O2, and O3 may be changed. However, the present disclosure is not limited thereto.

In accordance with some embodiments of the present disclosure, when the third selection input of selecting any one of the plural objects O2 and O3 displayed on the fourth region is received through the seventh sub-task, selection inputs for all of the plural objects may be deactivated. That is, the seventh sub-task may further include an operation of deactivating selection inputs for the plural objects O2 and O3 as receiving the third selection input. In this case, it is possible to prevent the test user from accidentally checking an incorrect answer by making a touch input unconsciously, so that the identification accuracy of the dementia identification model can be improved.

In accordance with some embodiments of the present disclosure, the processor 110 may perform a third preliminary task such that the test user may check a test related to the third task before performing the third task. Here, since the third preliminary task is performed in the same manner as the above-described third task, a detailed description thereof will be omitted.

The test result data obtained through the third preliminary task may not be used when training the dementia identification model, and only the test result data obtained in the third task may be used when training the dementia identification model. However, to increase the accuracy of the dementia identification of the dementia identification model, the test result data obtained in the third preliminary task may also be used when training the dementia identification model.

Meanwhile, the test result data obtained through the above-described third task may include at least one of information on the total time required to perform the third task the preset third number of times, information on the number of times determined as a correct answer through the seventh sub-task, information on the number of times determined as an incorrect answer through the seventh sub-task, and information on response time taken from performing the sixth sub-task until receiving the sixth selection input. However, to improve the accuracy of the dementia identification model, all of the total time information, the information on the number of times determined as a correct answer, the information on the number of times determined as an incorrect answer and the response time information may be included in the test result data.

In accordance with some embodiments of the present disclosure, a user in need of dementia identification may execute the memory test using his/her user terminal. In addition, the device 100 may obtain test result data generated by executing the memory test in the user terminal, and then input the data into a pre-trained dementia identification model to obtain a score value. In addition, the processor 110 may determine whether dementia is present, based on the magnitude of the score value, but the present disclosure is not limited thereto.

In accordance with some embodiments of the present disclosure, when training the dementia identification model, the dementia identification model may be trained by labeling the test result data, obtained after performing all of the first task related to the Stroop test, the second task related to a computational power test, and the third task related to a memory test, with a score value. In this case, the accuracy of the dementia identification model may be further improved. However, the present disclosure is not limited thereto, and the dementia identification model may be trained by labeling the test result data, obtained after performing at least two tasks of the first task, the second task, and the third task, with the score value.

The dementia identification model may be trained using the test result data obtained after performing all of the first task, the second task, and the third task. In this case, the user who needs dementia identification should perform all of the Stroop test, the computational power test and the memory test to improve the accuracy of dementia identification. That is, the processor 110 may obtain a score value by inputting the test result data, obtained by performing all of the Stroop test, the computational power test and the memory test, into the pre-trained dementia identification model. In addition, the processor 110 may determine whether dementia is present based on the magnitude of the score value. When determining whether dementia is present using the test result data obtained after performing all of the three tests, the accuracy of dementia identification of the dementia identification model may be significantly improved compared to the case that whether dementia is present is determined using test result data obtained after performing one test or two tests.

In the present disclosure, the test result data obtained after performing the first task, the second task, and the third task may be a digital biomarker having a high correlation coefficient with dementia identification among various types of digital biomarkers. Therefore, when determining whether dementia is present using the test result data obtained after performing the first task, the second task, and the third task, the accuracy of dementia identification may be improved.

In accordance with some embodiments of the present disclosure, the processor 110 of the device 100 may obtain user identification information prior to performing at least one test. Here, the user identification information may include user's age information, gender information, name, address information, and the like. In addition, at least a portion of the user identification information may be used as input data for training the dementia identification model together with the test result data. Specifically, age information and gender information may be used as input data for training of the dementia identification model together with the test result data. Also when identifying whether dementia is present using the training-completed dementia identification model, age information, gender information, and test result data may be used as input data. When training the dementia identification model using at least a portion of user identification information together with the test result data in such a manner, the accuracy of dementia identification may be further improved.

120 people in a cognitive normal group and 9 people in a cognitively impaired group conducted an experiment to identify whether they had dementia through their user terminal. The goal of this experiment was to confirm the accuracy of the pre-learned dementia identification model. Specifically, the test result data obtained by performing the Stroop test, a computational power test and a memory test was obtained through the user terminal, and whether dementia is present was determined based on the score value generated by inputting the test result data into the pre-trained dementia identification model according to some embodiments of the present disclosure. It was confirmed that the classification accuracy through the experiment was 80% or more.

According to at least one of the above-described several embodiments of the present disclosure, dementia may be accurately diagnosed in a method in which a patient hardly feels rejection.

In the present disclosure, the configurations and methods of the above-described several embodiments of the device 100 are not limitedly applied, and all or parts of each of the embodiments may be selectively combined to allow various modifications.

Various embodiments described in the present disclosure may be implemented in a computer or similar device-readable recording medium using, for example, software, hardware, or a combination thereof.

According to hardware implementation, some embodiments described herein may be implemented using at least one of Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, and other electrical units for performing functions. In some cases, some embodiments described in the present disclosure may be implemented with at least one processor.

According to software implementation, some embodiments such as the procedures and functions described in the present disclosure may be implemented as separate software modules. Each of the software modules may perform one or more functions, tasks, and operations described in the present disclosure. A software code may be implemented as a software application written in a suitable programming language. Here, the software code may be stored in the storage 120 and executed by at least one processor 110. That is, at least one program command may be stored in the storage 120, and the at least one program command may be executed by the at least one processor 110.

According to some embodiments of the present disclosure, the method of training the dementia identification model by at least one processor of a device may be implemented as code readable by the at least one processor in a recording medium readable by the at least one processor 110 provided in the device 100. The at least one processor-readable recording medium includes all types of recording devices in which data readable by the at least one processor 110 is stored. Examples of the at least one processor-readable recording medium includes Read Only Memory (ROM), Random Access Memory (RAM), CD-ROM, a magnetic tape, a floppy disk, an optical data storage device, and the like.

Meanwhile, although the present disclosure has been described with reference to the accompanying drawings, this is only an embodiment and the present disclosure is not limited to a specific embodiment. Various contents that can be modified by those of ordinary skill in the art to which the present disclosure belongs also belong to the scope of rights according to the claims. In addition, such modifications should not be understood separately from the technical spirit of the present disclosure.

The invention claimed is:

1. A method of training a neural network constituting a dementia identification model by at least one processor of a device, the method comprising:
   receiving, via a communication unit, user identification information of a test user from a test device of the test user;
   receiving, via the communication unit, test result data obtained by a first task related to Stroop test, a second task related to a computational power test, and a third task related to a memory test from the test device of the test user;
   labeling the test result data and the user identification information with a target score value; and
   training the dementia identification model by updating a weight of at least one node of the neural network by backpropagating, to an input layer of the neural network, a difference value between an output score value and the target score value,
   wherein the output score value is predicted through the neural network by inputting the test result data and the user identification data into the dementia identification model,
   wherein the target score value has a correlation with a paper score value obtained after the test user performs a Stroop test, a computational power test and a memory test through paper, and
   wherein the user identification information includes the test user's age information and the test user's gender information.

2. The method according to claim 1, wherein the first task comprises:
   a first sub-task that causes the test device of the test user to display a first number of numeric texts in a first region while interworking with displaying a first button for displaying a first numeral indicating the first number on a second region; and at least one second button for displaying a number different from the first number; and
   a second sub-task that determines whether an answer is correct according to a first selection input of selecting any one of the first button and the at least one second button.

3. The method according to claim 2, wherein the first task performs the first sub-task and the second sub-task a preset number of times while changing the first number and the numeric texts.

4. The method according to claim 2, wherein the second sub-task comprises:
an operation of determining an answer as a correct answer when the first selection input is an input of selecting the first button; or
an operation of determining an answer as an incorrect answer when the first selection input is an input of selecting any one of the at least one second button.

5. The method according to claim 3, wherein the test result data comprises at least one of information on a total time required to perform the first task a preset first number of times, information on a number of times determined as a correct answer through the second sub-task, information on a number of times determined as an incorrect answer through the second sub-task, and information on response time taken from performing the first sub-task until receiving the first selection input.

6. The method according to claim 1, wherein the second task comprises:
a third sub-task that causes the test device of the test user to display a third button comprising a first equation and a fourth button comprising a second equation when a fifth button comprising a preset text to be displayed between the third button and the fourth button; and
a fourth sub-task for determining whether an answer is correct according to a second selection input of selecting any one of the third button, the fourth button, and the fifth button.

7. The method according to claim 6, wherein the second task performs the third sub-task and the fourth sub-task a preset second number of times while changing the first equation and the second equation.

8. The method according to claim 6, wherein the fourth sub-task performs an operation of determining whether the second selection input is a correct answer based on a comparison result of a result value of the first equation and a result value of the second equation.

9. The method according to claim 7, wherein the test result data comprises at least one of information on a total time required to perform the second task a preset second number of times, information on the number of times determined as a correct answer through the fourth sub-task, information on the number of times determined as an incorrect answer through the fourth sub-task, and information on response time taken from performing the third sub-task until receiving the second selection input.

10. The method according to claim 1, wherein the third task comprises:
a fifth sub-task that causes the test device of the test user to display at least two objects for a preset time;
a sixth sub-task that causes the test device to display a first object of the at least two objects on a third region and to display a second object of the at least two objects and at least one additional object different from the at least two objects on a fourth region; and
a seventh sub-task that determines whether an answer is correct according to a third selection input of selecting any one from among a plural objects displayed on the fourth region.

11. The method according to claim 10, wherein the seventh sub-task further comprises an operation of deactivating selection inputs for the plural objects as receiving the third selection input.

12. The method according to claim 10, wherein the seventh sub-task comprises:
an operation of determining an answer as a correct answer when the third selection input is an input of selecting the second object; or
an operation of determining an answer as an incorrect answer when the third selection input is an input of selecting any one of the at least one additional object.

13. The method according to claim 10, wherein the third task performs the fifth sub-task, the sixth sub-task, and the seventh sub-task a preset third number of times while changing the at least two objects and the at least one additional object.

14. The method according to claim 13, wherein the test result data comprises at least one of information on a total time required to perform the third task the preset third number of times, information on a number of times determined as a correct answer through the seventh sub-task, information on a number of times determined as an incorrect answer through the seventh sub-task, and information on response time taken from performing the sixth sub-task until receiving the third selection input.

15. A computer program stored on a non-transitory computer-readable storage medium, wherein the computer program performs steps of training a neural network constituting a dementia identification model when executed by at least one processor of a device, the steps comprising:
receiving, via a communication unit, user identification information of a test user from a test device of the test user;
obtaining receiving, via the communication unit, test result data through at least one of obtained by a first task related to Stroop test, a second task related to a computational power test, and a third task related to a memory test from the test device of the test user;
labeling the test result data and the user identification information with a target score value; and
training the dementia identification model by updating a weight of at least one node of the neural network by backpropagating, to an input layer of the neural network, a difference value between an output score value and the target score value,
wherein the output score value is predicted through the neural network by inputting the test result data and the user identification information into the dementia identification model,
wherein the target score value has a correlation with a paper score value obtained after the test user performs a Stroop test, a computational power test and a memory test through paper, and
wherein the user identification information includes the test user's age information and the test user's gender information.

16. A device for training a neural network constituting a dementia identification model, the device comprising:
a storage configured to store at least one program command;
a communication unit; and
at least one processor configured to perform the at least one program command,
wherein the at least one processor receives, via the communication unit, user identification information of a test user from a test device of the test user, receives, via the communication unit, test result data obtained by a first task related to Stroop test, a second task related to a computational power test, and a third task related to a memory test from the test device of the test user, labels the test result data and the user identification information with a score value, and trains the dementia identification model by updating a weight of at least one node of the neural network by backpropagating, to an input layer of the neural network, a difference value between an output score value and the target score value, wherein the output score value is predicted through the neural network by inputting the test result data and the user identification information into the dementia identification model, wherein the target score value has a correlation with a paper score value obtained after the test user performs a Stroop test, a computational power test and a memory test through paper, and wherein the user identification information includes the test user's age information and the test user's gender information.

* * * * *